US00PP36940P2

(12) United States Plant Patent
Bentley

(10) Patent No.: US PP36,940 P2
(45) Date of Patent: Sep. 2, 2025

(54) ***LAVANDULA* PLANT NAMED 'IB510-17'**

(50) Latin Name: *Lavandula pedunculata*
Varietal Denomination: IB510-17

(71) Applicant: Howard Bentley, Wonga Park (AU)

(72) Inventor: Howard Bentley, Wonga Park (AU)

(73) Assignee: PLANT GROWERS AUSTRALIA PTY. LTD., Wonga Park (AU)

( * ) Notice: Subject to any disclaimer, the term of this patent is extended or adjusted under 35 U.S.C. 154(b) by 0 days.

(21) Appl. No.: 18/914,862

(22) Filed: Oct. 14, 2024

(51) Int. Cl.
*A01H 6/50* (2018.01)
*A01H 5/02* (2018.01)

(52) U.S. Cl.
USPC ..... Plt./445

(58) Field of Classification Search
USPC ..... Plt./445
CPC ..... A01H 6/502; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Lavandula* plant named 'IB510-17', characterized by its relatively compact and upright to somewhat outwardly plant habit; freely branching growth habit, dense and bushy appearance; freely flowering habit; violet-colored flowers with large light purple-colored sterile flower bracts arranged on short terminal spikes; relatively short peduncles; and good garden performance.

2 Drawing Sheets

Figure 1:
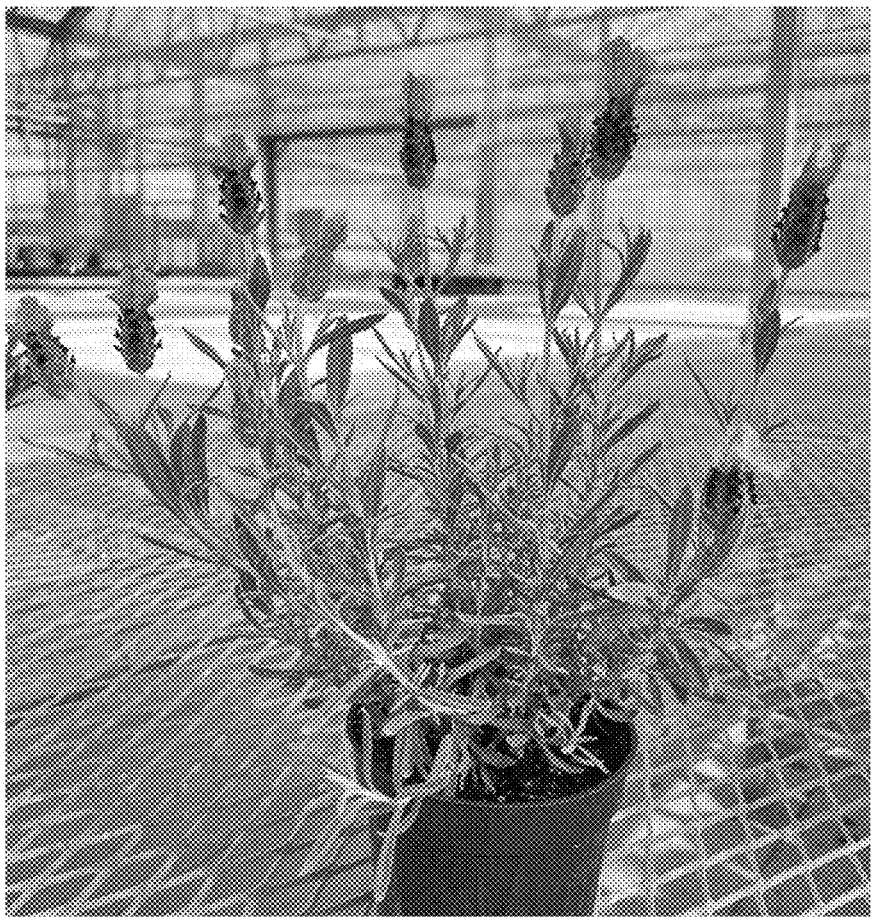

Botanical designation: *Lavandula pedunculata.*
Cultivar denomination: 'IB510-17'.

BACKGROUND OF THE INVENTION

The present invention relates to a new and distinct *Lavandula* plant, botanically known as *Lavandula pedunculata*, commonly referred to as French Lavender and hereinafter referred to by the name 'IB510-17'.

The new *Lavandula* plant is a product of a planned breeding program conducted by the Inventor in Wonga Park, Victoria, Australia. The objective of the breeding program was to develop new dense and freely-flowering *Lavandula* plants with silvery foliage, attractive flower coloration, relatively short peduncles and good garden performance.

The new *Lavandula* plant originated from a self-pollination in October 2014 of *Lavandula pedunculata* 'Fine Silver Pink', not patented. The new *Lavandula* plant was discovered and selected by the Inventor as a single flowering plant within the progeny of the stated self-pollination in a controlled greenhouse environment in Wonga Park, Victoria, Australia in October 2015.

Asexual reproduction of the new *Lavandula* plant by softwood terminal cuttings in a controlled greenhouse environment in Wonga Park, Victoria, Australia since December 2015 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'IB510-17' as a new and distinct *Lavandula* plant:

1. Relatively compact and upright to somewhat outwardly plant habit.
2. Freely branching growth habit, dense and bushy appearance.
3. Freely flowering habit.
4. Violet-colored flowers with large light purple-colored sterile flower bracts arranged on short terminal spikes.
5. Relatively short peduncles.
6. Good garden performance.

Plants of the new *Lavandula* differ primarily from plants of the parent, 'Fine Silver Pink', in sterile flower bract color as plants of the new *Lavandula* have light purple-colored sterile flower bracts whereas plants of 'Fine Silver Pink' have pink-colored sterile flower bracts.

Plants of the new *Lavandula* differ primarily from plants of *Lavandula pedunculata*, 'Iceberry Ruffles', not patented, in the following characteristics:

1. Plants of the new *Lavandula* are not as compact as plants of 'Iceberry Ruffles'.
2. Plants of the new *Lavandula* have longer sterile flower bracts than plants of 'Iceberry Ruffles'.
3. Plants of the new *Lavandula* have slightly longer peduncles than plants of 'Iceberry Ruffles'.

Plants of the new *Lavandula* can also be compared to plants of *Lavandula stoechas* 'Silver Anouk', disclosed in U.S. Plant Pat. No. 20,068. In side by side comparisons, plants of the new *Lavandula* and 'Silver Anouk' differ primarily in the following characteristics:

1. Plants of the new *Lavandula* are denser than plants of 'Silver Anouk'.
2. Plants of the new *Lavandula* have broader and longer sterile flower bracts than plants of 'Silver Anouk'.

3. Sterile flower bracts of plants of the new *Lavandula* are more intense purple in color than sterile flower bracts of plants of 'Silver Anouk'.

BRIEF DESCRIPTION OF THE PHOTOGRAPHS

The accompanying photographs illustrate the overall appearance of the new *Lavandula* plant showing the colors as true as it is reasonably possible to obtain in colored reproductions of this type. Colors in the photographs may differ slightly from the color values cited in the detailed botanical description which accurately describe the colors of the new *Lavandula* plant.

The photograph on the first sheet (FIG. 1) is a side perspective view of a typical flowering plant of 'IB510-17' grown in a container.

Figure 2:
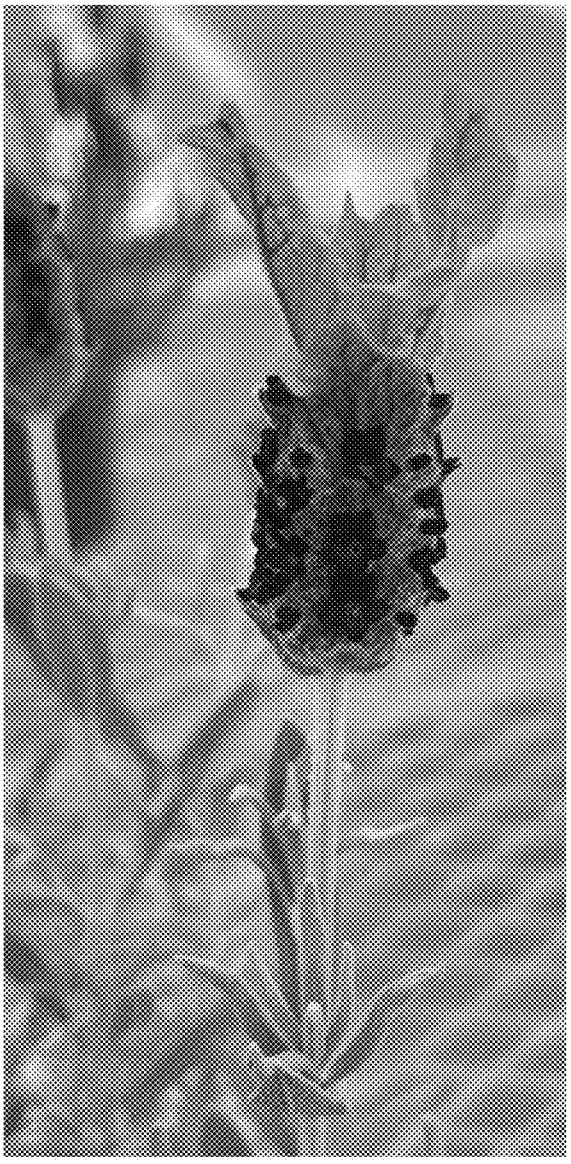

The photograph on the second sheet (FIG. 2) is a close-up view of a typical inflorescence of 'IB510-17'.

DETAILED BOTANICAL DESCRIPTION

The aforementioned photographs and following observations, measurements and values describe plants grown during the spring in Elburn, Illinois and under cultural practices typical of commercial *Lavandula* production. Plants were four months old when the photographs and the description were taken. In the description, color references are made to The Royal Horticultural Society Colour Chart, 2015 Edition, except where general terms of ordinary dictionary significance are used.

Botanical classification: *Lavandula pedunculata* 'IB510-17'.

Parentage:

*Female, or seed, parent.*—*Lavandula pedunculata* 'Fine Silver Pink', not patented.

*Male, or pollen, parent.*—*Lavandula pedunculata* 'Fine Silver Pink', not patented.

Propagation:

*Type*.—Terminal softwood vegetative cuttings.

*Time to initiate roots, summer*.—About ten days at temperatures about 24° C.

*Time to initiate roots, winter*.—About twelve days at temperatures about 21° C.

*Time to produce a rooted young plant, summer*.—About 24 to 28 days at temperatures ranging from 23° C. to 26° C.

*Time to produce a rooted young plant, winter*.—About 35 to 40 days at temperatures ranging from 15° C. to 18° C.

*Root description*.—Fine, fibrous; typically white to light brown in color, actual color of the roots is dependent on substrate composition, water quality, fertilizer type and formulation.

*Rooting habit*.—Freely branching; medium density.

Plant description:

*Plant and growth habit*.—Herbaceous perennial; relatively compact and upright to somewhat outwardly plant habit; roughly inverted triangular in overall shape; moderately vigorous growth habit and moderate growth rate; flowers arranged in verticillasters on terminal spikes; freely branching habit, dense and bushy appearance.

*Plant height, soil level to top of foliar plane*.—About 19 cm to 21 cm.

*Plant height, soil level to top of floral plane*.—About 23 cm to 25 cm.

*Plant width*.—About 20 cm to 23 cm.

*Lateral branch description*.—Quantity per plant: About 12 to 15 primary lateral branches each with potentially two secondary branches developing at every node during the flowering season. Length: About 17 cm to 19 cm. Diameter: About 2 mm. Internode length: About 1.8 cm to 2.4 cm. Strength: Moderately strong; flexible. Aspect: Mostly upright to slightly outwardly. Texture and luster: Densely tomentose; slightly glossy. Color, developing: Close to 144A to 144B. Color, developed: Close to 144B to 144C; if woody, close to N199A to N199B.

*Leaf description*.—Arrangement: Opposite, simple; sessile. Length, largest leaves: About 3.8 cm to 4 cm. Width, largest leaves: About 7 mm to 8 mm. Shape: Linear. Apex: Acute to acuminate. Base: Cuneate. Margin: Entire; moderately revolute. Texture and luster, upper and lower surfaces: Densely pubescent; matte. Fragrance: Strongly aromatic, pungent. Venation pattern: Pinnate. Color: Developing leaves, upper surface: Close to 137B. Developing leaves, lower surface: Close to 138A to 138B. Fully expanded leaves, upper surface: Close to NN137B to NN137C; venation, close to 144A; pubescence, close to 157A. Fully expanded leaves, lower surface: Close to 138A to 138B; venation, close to 138B; pubescence, close to 157A.

Flower description:

*Flower type, arrangement and habit*.—Small single salverform flowers arranged in verticillasters on terminal compact cylindrical spikes; freely flowering habit with about 84 to 96 flowers developing in stacked whorls per inflorescence and numerous inflorescences developing per plant during the flowering season; flowers with two-lobed upper lip and three-lobed lower lip; flowers face mostly upright to outwardly on the spike.

*Natural flowering season*.—Relatively long flowering period; continuous from late winter to late spring/early summer in Australia.

*Flower longevity on the plant*.—Inflorescences last about one month on the plant; flowers not persistent.

*Fragrance*.—Resinous, pungent.

*Flower buds*.—Length: About 1.25 cm. Diameter: About 7 mm. Shape: Conical. Texture: Densely tomentose. Color: Close to 76A; pubescence, close to 157A.

*Inflorescence diameter*.—About 1.25 cm to 1.4 cm, excluding terminal bracts.

*Flower diameter*.—About 2 mm to 3 mm.

*Flower length, including tube*.—About 7 mm to 7.5 mm.

*Flower tube length*.—About 6 mm; free part, about 1 mm to 1.5 mm.

*Flower tube diameter, distally*.—About 2 mm.

*Flower tube diameter, proximally*.—About 1 mm.

*Petals*.—Quantity and arrangement: Upper lip, two-lobed and lower lip, three-lobed, fused into a narrow tube. Length, upper and lower lips, free part: About 1 mm. Width, upper and lower lips, free part: Less than 1 mm. Shape, upper lip: Obovate. Shape, lower lip: Ovate. Apex, upper and lower lips: Obtuse, rounded. Margin, upper and lower lips, free part: Entire. Texture and luster, upper (inner) surface, upper and lower lips: Smooth, glabrous; slightly velvety; slightly glossy. Texture and luster, lower (outer) surface, upper and lower lips: Smooth, glabrous; slightly velvety; matte. Color, upper and lower lips, free part: When opening and fully opened, upper (inner) surface: Close to 86A. When opening and fully opened, lower (outer) surface: Close to 86B. Color, tube, inner surface: Close to 86A. Color, tube, outer surface: Close to 86A and 86B.

*Basal flower bracts*.—Quantity and arrangement: Each cluster of about six to eight flowers is subtended by a single basal flower bract. Length: About 1 cm. Width: About 9 mm. Shape: Roughly cordate. Apex: Long cuspidate. Base: Truncate with cordate tendencies. Margin: Entire; slightly undulate giving a slightly ruffled appearance. Texture and luster, upper surface: Mostly smooth and glabrous with pubescence along marginal edges; slightly glossy. Texture and luster, lower surface: Mostly smooth and glabrous with pubescence along marginal edges; matte. Color, upper and lower surfaces: Translucent, close to NN155D with reticulate venation, close to 143A.

*Sterile flower bracts*.—Quantity and arrangement: About five to six sterile flower bracts at apex of spike; bracts variable in size and shape. Length, largest bracts: About 2.2 cm to 2.7 cm. Width, largest bracts: About 1.5 cm to 1.7 cm. Shape: Obovate; ruffled appearance. Apex: Obtuse with acute tendencies. Base: Cuneate. Margin: Entire; undulate giving a ruffled appearance. Texture and luster, upper surface: Smooth, glabrous; slightly glossy. Texture and luster, lower surface: Smooth, glabrous; matte. Color, upper surface: Close to 85A; venation, close to 143A; color does not change with subsequent development. Color, lower surface: Close to 85A to 85B; venation, close to 143A; color does not change with subsequent development.

*Sepals*.—Quantity and arrangement: Five, fused into a campanulate tube. Calyx length: About 7 mm to 8 mm. Calyx diameter: About 2 mm to 3 mm. Shape: Lanceolate. Apex: Obtuse. Margin: Entire. Texture and luster, upper (inner) surface: Smooth, glabrous; slightly glossy. Texture and luster, lower (outer) surface: Densely pubescent; matte. Color, upper (inner) surface: Close to 143A. Color, lower (outer) surface: Close to N148B to N148C.

*Peduncles*.—Length: About 4.5 cm to 5.5 cm. Diameter: About 2 mm. Aspect: Mostly upright. Strength: Moderately strong; flexible. Texture and luster: Pubescent; matte. Color: Close to 144A to 144B.

*Reproductive organs*.—Stamens: Quantity per flower: Four. Anther shape: Reniform. Anther color: Close to 157C. Pollen amount: None observed. Pistils: Quantity per flower: One. Stigma shape: Club-shaped. Stigma color: Close to N79A. Ovary color: Close to 143A to 143B.

*Seeds and fruits*.—To date, seed and fruit production has not been observed on plants of the new *Lavandula*.

Pathogen & pest resistance: To date, plants of the new *Lavandula* have not been observed to be resistant to pathogens and pests common to *Lavandula* plants.

Garden performance: Plants of the new *Lavandula* have exhibited good garden performance and to tolerate rain and wind and temperatures ranging from about 1° C. to about 40° C.

It is claimed:

1. A new and distinct *Lavandula* plant named 'IB510-17' as herein illustrated and described.

* * * * *